United States Patent
Al-Khattaf et al.

(10) Patent No.: US 8,435,909 B2
(45) Date of Patent: May 7, 2013

(54) DUAL-ZEOLITE CATALYST FOR PRODUCTION OF ETHYLBENZENE

(75) Inventors: Sulaiman S. Al-Khattaf, Dhahran (SA); Taiwo Odedairo, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 500 days.

(21) Appl. No.: 12/656,905

(22) Filed: Feb. 18, 2010

(65) Prior Publication Data
US 2011/0201864 A1 Aug. 18, 2011

(51) Int. Cl.
*B01J 29/06* (2006.01)
*B01J 27/182* (2006.01)

(52) U.S. Cl.
USPC .......... 502/67; 502/63; 502/64; 502/71; 502/73; 502/77; 502/78; 502/214

(58) Field of Classification Search .......... 502/63, 502/64, 67, 71, 73, 77, 78, 214
See application file for complete search history.

(56) References Cited

U.S. PATENT DOCUMENTS

| | | | |
|---|---|---|---|
| 4,169,111 A | 9/1979 | Wight | |
| 4,818,739 A * | 4/1989 | Gortsema et al. | 502/67 |
| 4,867,861 A * | 9/1989 | Abdo et al. | 208/27 |
| 4,880,760 A * | 11/1989 | Pellet et al. | 502/67 |
| 4,975,401 A * | 12/1990 | Kaeding et al. | 502/67 |
| 5,039,640 A * | 8/1991 | Absil et al. | 502/67 |
| 5,177,280 A | 1/1993 | Juguin et al. | |
| 5,430,211 A | 7/1995 | Pogue et al. | |
| 5,853,566 A * | 12/1998 | Kraushaar-Czarnetzki et al. | 208/109 |
| 5,998,687 A | 12/1999 | Woodle et al. | |
| 6,093,866 A * | 7/2000 | Wang et al. | 585/467 |
| 6,133,186 A * | 10/2000 | Gosselink et al. | 502/67 |
| 6,716,784 B2 * | 4/2004 | Corma Canos et al. | 502/67 |
| 6,831,203 B1 | 12/2004 | Mohr et al. | |
| 6,858,556 B2 * | 2/2005 | Kuvettu et al. | 502/67 |
| 7,393,805 B2 * | 7/2008 | Boldingh et al. | 502/63 |
| 7,419,931 B2 * | 9/2008 | Serra et al. | 502/64 |
| 2003/0036670 A1 * | 2/2003 | Oh et al. | 585/400 |
| 2005/0038307 A1 * | 2/2005 | Van der Aalst et al. | 585/475 |
| 2005/0065017 A1 * | 3/2005 | McMinn et al. | 502/64 |
| 2005/0234279 A1 * | 10/2005 | Serra et al. | 585/475 |
| 2005/0245781 A1 * | 11/2005 | Martens et al. | 585/640 |
| 2006/0100471 A1 * | 5/2006 | Serra Alfaro et al. | 585/475 |
| 2007/0055086 A1 * | 3/2007 | Buchanan et al. | 585/475 |
| 2007/0185356 A1 * | 8/2007 | Boldingh et al. | 585/475 |
| 2007/0293714 A1 * | 12/2007 | Long et al. | 585/899 |
| 2008/0154081 A1 * | 6/2008 | Elia et al. | 585/467 |
| 2009/0299115 A1 * | 12/2009 | Guillon et al. | 585/481 |
| 2010/0029467 A1 * | 2/2010 | Inui et al. | 502/66 |

FOREIGN PATENT DOCUMENTS

MX 9502428 2/1997

OTHER PUBLICATIONS

Burdick, D. L. and Leffler, W. L., Petrochemicals in NonTechnical Language, 3rd ed., Pennwell Corporation, Tulsa, OK (2007), pp. 119-124.
Green, m. M. and Wittcoff, H. H., Organic Chemistry Principles and Industrial Practice, Wiley-VCH GmbH & Co. (2003), pp. 52-54.

* cited by examiner

*Primary Examiner* — Elizabeth Wood
(74) *Attorney, Agent, or Firm* — Richard C. Litman

(57) ABSTRACT

The dual-zeolite catalyst for production of ethylbenzene is formed by mixing at least two different zeolites selected from mordenite, beta, ZSM-5, ZSM-11, ZSM-12, ZSM-22, ZSM-23, MFI topology zeolite, NES topology zeolite, EU-1, SAPO-5, SAPO-34, SAPO-11 and MAPO-36 zeolites and an inactive alumina binder. The two zeolites have different topology and possess dissimilar and unique physical and chemical characteristics, including particle size, surface area, pore size and acidity. The preferred amount of the two zeolites may range from 10 to 90 wt % of the total catalyst amount in the final dried and calcined form, preferably the zeolites are in equal parts by weight.

4 Claims, No Drawings

DUAL-ZEOLITE CATALYST FOR PRODUCTION OF ETHYLBENZENE

BACKGROUND OF THE INVENTION

1. Field of the Invention

The present invention relates to processes for the alkylation of aromatics and processes for the production of ethylbenzene, and particularly to a dual-zeolite catalyst for the production of ethylbenzene.

2. Description of the Related Art

Ethylbenzene is used in the production of styrene. For this reason, most ethylbenzene plants are located close to styrene plants. Commercially, two processes are used to produce ethylbenzene.

The first process involves reaction of ethylene with benzene in the presence of an aluminum trichloride catalyst and hydrochloric acid in a Friedel-Crafts reaction, which may be done either in the liquid or the vapor phase. Although widely used, the Friedel-Crafts process has some drawbacks. The process does not stop at mono-substitution, but also produces diethylbenzene and triethylbenzene. Further, the spent catalyst cannot be used again. The cost of disposing of the catalyst is high, and has associated environmental problems with wastewater due to the corrosive nature of the materials.

The second process is usually a two-step process involving the dehydrogenation of ethane using a first zeolite to produce ethylene, followed by reaction of the ethylene with benzene in the presence of a second zeolite. The zeolite catalysts are non-corrosive, reducing environmental and disposal problems, and the zeolites selectively produce ethylbenzene to the exclusion of polysubstituted benzene. However, the low yield from the process makes the process expensive.

Thus, a dual-zeolite catalyst for the production of ethylbenzene solving the aforementioned problems is desired.

SUMMARY OF THE INVENTION

The dual-zeolite catalyst for production of ethylbenzene is formed by mixing at least two different zeolites selected from mordenite, beta, ZSM-5, ZSM-11, ZSM-12, ZSM-22, ZSM-23, MFI topology zeolite, NES topology zeolite, EU-1, SAPO-5, SAPO-34, SAPO-11 and MAPO-36 zeolites and an inactive alumina binder. The two zeolites have different topology and possess dissimilar and unique physical and chemical characteristics, including particle size, surface area, pore size and acidity. The preferred amount of the two zeolites may range from 10 to 90 wt % of the total catalyst amount in the final dried and calcined form, preferably the zeolites are in equal parts by weight.

A refractory binder or matrix is optionally utilized to facilitate fabrication of the catalyst and to provide strength. The binder should be uniform in composition and relatively refractory to the conditions used in the process. Suitable binders include inorganic oxides, such as one or more of alumina, magnesia, zirconia, chromia, titania, boria, phosphate, zinc oxide and silica. Alumina is a preferred binder. The two zeolites are mixed with the alumina binder in dry powdered form to yield a homogeneous mixture to ensure homogeneous composition of the extrudates formed.

An exemplary catalyst includes mordenite and ZSM-5 zeolite. The benzene conversion reaction may be conducted for experimental purposes in a riser simulator or fast fluidized reactor at 200-500° C., at a pressure of 1.0 atmospheric to 5.0 atmospheres, and using a benzene and ethanol mixture as a feed in a molar ratio of 1 to 5. This riser simulator produces an environment nearly identical to those found in large-scale industrial reactors, providing an accurate, quick and an effective method for evaluating catalyst performance. The feed stream to the conversion process generally comprises benzene and ethanol, and permits effective ethylation of benzene into an alkylbenzene, preferably ethylbenzene. The feed stream is preferably reacted in the vapor phase. The ethylation reaction preferably yields a product having a high ethylbenzene content, and a low content of diethylbenzene isomers. The catalyst, as tested in a riser simulator for ethylation reaction using a benzene and ethanol feed mixture, demonstrates the effectiveness of the catalyst for benzene conversion and selective production of ethylbenzene.

These and other features of the present invention will become readily apparent upon further review of the following specification.

DETAILED DESCRIPTION OF THE PREFERRED EMBODIMENTS

The dual-zeolite catalyst for production of ethylbenzene is formed by mixing at least two different zeolites selected from mordenite, beta, ZSM-5, ZSM-11, ZSM-12, ZSM-22, ZSM-23, MFI topology zeolite, NES topology zeolite, EU-1, SAPO-5, SAPO-34, SAPO-11 and MAPO-36 zeolites and an inactive alumina binder. The two zeolites have different topology and possess dissimilar and unique physical and chemical characteristics, including particle size, surface area, pore size and acidity. The preferred amount of the two zeolites may range from 10 to 90 wt % of the total catalyst amount in the final dried and calcined form, preferably the zeolites are in equal parts by weight.

A refractory binder or matrix is optionally utilized to facilitate fabrication of the catalyst and to provide strength. The binder should be uniform in composition and relatively refractory to the conditions used in the process. Suitable binders include inorganic oxides, such as one or more of alumina, magnesia, zirconia, chromia, titania, boria, phosphate, zinc oxide and silica. Alumina is a preferred binder. The two zeolites are mixed with the alumina binder in dry powdered form to yield a homogeneous mixture to ensure homogeneous composition of the extrudates formed.

An exemplary catalyst includes mordenite and ZSM-5 zeolite. The benzene conversion reaction may be conducted for experimental purposes in a riser simulator or fast fluidized reactor at 200-500° C., at a pressure of 1.0 atmospheric to 5.0 atmospheres, and using a benzene and ethanol mixture as a feed in a ratio of 1 to 5. This riser simulator produces an environment nearly identical to those found in large-scale industrial reactors, providing an accurate, quick and an effective method for evaluating catalyst performance. The feed stream to the conversion process generally comprises benzene and ethanol, and permits effective ethylation of benzene into an alkylbenzene, preferably ethylbenzene. The feed stream is preferably reacted in the vapor phase. The ethylation reaction preferably yields a product having a high ethylbenzene content, and a low content of diethylbenzene isomers. The catalyst, as tested in a riser simulator for ethylation reaction using a benzene and ethanol feed mixture, demonstrates the effectiveness of the catalyst for benzene conversion and selective production of ethylbenzene.

The dual-zeolite catalyst will now be illustrated by the following examples by way of exemplification, and not for purposes of limitation. The catalyst of Example 1 is an exemplary embodiment only, and is not intended to limit the general description of the dual-zeolite-based catalyst as described above.

Example 1

Dry powder of one (1) part by weight of the uncalcined proton form of mordenite (H-mordenite) (HSZ-690HOA, obtained from Tosoh Chemicals, Japan, having a silica-to-alumina molar ratio of 240) was mixed with one (1) part by weight of the uncalcined proton form of ZSM-5 (CT-405, obtained from CATAL, UK, having a silica-to-alumina molar ratio of 30) and with one (1) part by weight of uncalcined alumina binder (Cataloid AP-3, obtained from CCIC, Japan) at room temperature. The dry powdered mixture of mordenite, ZSM-5 and alumina was thoroughly agitated to produce a homogenously mixed powdered catalyst. The mixture was then pressed in a round steel die under high pressure to produce a disk, which was broken into small pieces that were sieved to produce granules ranging in size from 1.0-1.5 mm. The composition of the granules in weight ratio was as follows: H-mordenite:H-ZSM-5:AP-3 (1:1:1), and the weight percent of each of H-mordenite, H-ZSM-5 and alumina was 33.3%.

Example 2

The catalyst of the Example 1 was tested for ethylation reaction using a benzene and ethanol feed mixture (both Analytical grade, 99% pure obtained from Sigma-Aldrich) in a molar ratio of 1:1 to demonstrate effectiveness of the catalysts for benzene conversion and production of ethylbenzene. Catalytic experiments were carried out in the riser simulator with a feed mixture of benzene and ethanol for residence times of 3, 5, 7, 10, 13, 15 and 20 seconds at 250° C. reaction temperatures. 800 mg of the catalyst was weighed and loaded into the riser simulator basket. The system was then sealed and tested for any pressure leaks by monitoring the pressure changes in the system.

Furthermore, the reactor was heated to the desired reaction temperature. The vacuum box was also heated to 250° C. and evacuated to a pressure of 0.5 psi to prevent any condensation of hydrocarbons inside the box. The heating of the riser simulator was conducted under continuous flow of inert gas (Argon), and it usually takes a few hours until thermal equilibrium is finally attained.

Meanwhile, before the initial experimental run, the catalyst was activated for 15 minutes at 620° C. in a stream of Ar. The temperature controller was set to the desired reaction temperature, and in the same manner, the timer was adjusted to the desired reaction time. At this point, the gas chromatograph was started and set to the desired conditions. Once the reactor and the gas chromatograph reached the desired operating conditions, 200 µl (microliter) of the feed was injected directly into the reactor via a loading syringe. At the end of specified residence time, the four-port valve was opened immediately, ensuring that the reaction was terminated and the entire product stream was sent on-line to the analytical equipment via a preheated vacuum box chamber.

The products were analyzed in an Agilent 6890N gas chromatograph with a flame ionization detector and a capillary column of INNOWAX, 60-m cross-linked methyl silicone with an internal diameter of 0.32 mm. Table 1 shows benzene conversion and ethylbenzene selectivity results obtained for catalyst of Example 1 at 250° C. reaction temperatures. The compositional analysis results for the reaction products shows the reproducibility of the conversion reaction within ±1%.

For purposes of expressing the results, benzene conversion weight percent was calculated as the difference in the benzene weight percent of the feed and the benzene weight percent of the product, the difference being multiplied by 100 and divided by the benzene weight percent of the feed. The ethylbenzene selectivity was calculated as the weight percent of ethylbenzene in the product multiplied by 100 and divided by the benzene conversion weight percent.

TABLE 1

| Reaction temperature of 250° C. | | | | | | | |
|---|---|---|---|---|---|---|---|
| Reaction Temperature | 250 | 250 | 250 | 250 | 250 | 250 | 250 |
| Time-On-Stream (sec) | 3 | 5 | 7 | 10 | 13 | 15 | 20 |
| Benzene Conversion | 1.1 | 3.2 | 5.0 | 8.5 | 11.7 | 12.5 | 17.3 |
| Ethylbenzene Selectivity | 95.6 | 85.4 | 81.9 | 74.5 | 73.5 | 72.5 | 70.9 |

Example 3

This example illustrates the production of ethylbenzene from ethylation reaction of benzene and ethanol using the catalyst of Example 1 at 275° C. reaction temperature. Following the procedure of Example 2 for evaluation of the catalyst, the ethylation reaction was carried out at 275° C. The catalytic reaction conditions of the amount of feed, the weight of the catalyst, the residence time, the reaction pressure, and the product analysis conditions were similar to those described in Example 2. Table 2 shows benzene conversion and ethylbenzene selectivity results obtained for the catalyst of Example 1 at 275° C. reaction temperature.

TABLE 2

| Reaction temperature of 275° C. | | | | | | | |
|---|---|---|---|---|---|---|---|
| Reaction Temperature | 275 | 275 | 275 | 275 | 275 | 275 | 275 |
| Time-On-Stream (sec) | 3 | 5 | 7 | 10 | 13 | 15 | 20 |
| Benzene Conversion | 3.0 | 5.7 | 8.7 | 11.7 | 14.1 | 16.8 | 20.0 |
| Ethylbenzene Selectivity | 84.1 | 73.9 | 72.5 | 71.4 | 70.6 | 71.6 | 67.6 |

Example 4

This example illustrates the production of ethylbenzene from the ethylation reaction of benzene and ethanol using the catalyst of Example 1 at 300° C. reaction temperature. Following the procedure of Example 2 for evaluation of the catalyst, the ethylation reaction was carried out at 300° C. The catalytic reaction conditions of the amount of feed, the weight of the catalyst, the residence time, the reaction pressure, and the product analysis conditions were similar to those described in Example 2. Table 3 shows benzene conversion and ethylbenzene selectivity results obtained for the catalyst of Example 1 at 300° C. reaction temperature.

TABLE 3

| Reaction Temperature of 300° C. | | | | | | | |
|---|---|---|---|---|---|---|---|
| Reaction Temperature | 300 | 300 | 300 | 300 | 300 | 300 | 300 |
| Time-On-Stream | 3 | 5 | 7 | 10 | 13 | 15 | 20 |
| Benzene Conversion | 3.4 | 6.7 | 9.3 | 14.5 | 18.4 | 19.4 | 23.3 |
| Ethylbenzene Selectivity | 73.5 | 72.3 | 70.8 | 69.6 | 70.2 | 68.4 | 67.2 |

Comparing the data in Tables 1, 2 and 3 at the three reaction temperatures 250° C., 275° C. and 300° C., it is evident that benzene conversion increased with temperature and reached the 23.3% level at 300° C. using the catalyst of Example 1. It is quite evident and clear that the dual-zeolite catalyst shows a high percent benzene conversion. Likewise, comparing the data in Tables 1, 2 and 3 at the three reaction temperatures 250° C., 275° C. and 300° C., it is apparent that the ethylbenzene selectivity is quite high (95.6%) at 250° C. using the catalyst of Example 1. It is quite evident and clear that the dual-zeolite catalyst high selectivity for ethylbenzene formation.

It is to be understood that the present invention is not limited to the embodiments described above, but encompasses any and all embodiments within the scope of the following claims.

We claim:

1. A dual-zeolite catalyst for the production of ethylbenzene, consisting essentially of:
   a first zeolite and a second zeolite selected from the group of zeolites consisting of mordenite, beta, ZSM-5, ZSM-11, ZSM-12, ZSM-22, ZSM-23, MFI topology zeolite, NES topology zeolite, EU-1, SAPO-5, SAPO-34, SAPO-11 and MAPO-36, the second zeolite being a different member of the group from the first zeolite; and
   an uncalcined alumina binder binding the first and second zeolites together, wherein a ratio by weight of the first zeolite to the second zeolite to the uncalcined alumina binder is 1:1:1, the first zeolite, the second zeolite and the uncalcined alumina binder being homogeneously mixed.

2. The dual-zeolite catalyst according to claim 1, wherein the first zeolite comprises mordenite and the second zeolite comprises ZSM-5.

3. The dual-zeolite catalyst according to claim 1, wherein said mordenite has a silica-to-alumina molar ratio of about 240.

4. The dual-zeolite catalyst according to claim 1, wherein said ZSM-5 has a silica-to-alumina molar ratio of about 30.

* * * * *